United States Patent [19]

White et al.

[11] Patent Number: 4,542,227

[45] Date of Patent: Sep. 17, 1985

[54] PROCESSES FOR THE PREPARATION OF SPECTINOMYCIN ANALOGS, NOVEL PRODUCTS AND INTERMEDIATES THEREIN

[75] Inventors: David R. White, Kalamazoo, Mich.; Clarence J. Maring, New Haven, Conn.

[73] Assignee: The Upjohn Company, Kalamazoo, Mich.

[21] Appl. No.: 588,176

[22] Filed: Mar. 12, 1984

Related U.S. Application Data

[62] Division of Ser. No. 381,113, May 24, 1982, Pat. No. 4,467,103.

[51] Int. Cl.$^4$ ............................................ C07H 17/04
[52] U.S. Cl. ........................................................ 549/361
[58] Field of Search ........................................ 549/361

[56] References Cited

U.S. PATENT DOCUMENTS 3,234,092  2/1966  Bergy et al. ............................ 435/80
4,282,152  8/1981  White .................................... 549/361
4,420,624  12/1983  White et al. ........................ 549/361

OTHER PUBLICATIONS

March, "The Mannich Reaction", Advanced Organic Chemistry: Reactions, Mechanisms and Structure, pp. 670-672, McGraw-Hill Book Company (1968).
Flick, "The Use of a Mannich Base as a Source of an Unsaturated Ketone for Condensations with an Active Methylene Compound", Organic Reactions, vol. 1, pp. 320-322, New York: John Wiley and Sons, Inc. (1942).
Brewster et al., "Alkylations with Tertiary Amines", Organic Reactions, vol. 7, pp. 126-130, New York: John Wiley and Sons, Inc. (1953).
Bergman et al., "Robinson's Modification of the Michael Condensation", Organic Reactions, vol. 10, pp. 222-223: New York, John Wiley and Sons, Inc. (1959).
March, Advanced Organic Chemistry: Reactions, Mechanisms, and Structure, pp. 199-200 and pp. 287-290, McGraw-Hill Book Co. (1968).
Cram et al., Organic Chemistry, pp. 272-291, McGraw-Hill Book Co. (1964).

*Primary Examiner*—Ethel G. Love
*Attorney, Agent, or Firm*—Sidney B. Williams, Jr.; Joan Thierstein; Paul J. Koivuniemi

[57] ABSTRACT

The present invention relates to novel methods of preparing a wide variety of spectinomycin analogs and biologically acceptable salts thereof. Further, the invention relates both to novel intermediates and novel products therein. The novel products are spectinomycin analogs which can be used for the same biological purposes as spectinomycin. The processes of the invention provide for novel intermediates that are versatile and highly reactive exocyclic enones.

3 Claims, No Drawings

PROCESSES FOR THE PREPARATION OF SPECTINOMYCIN ANALOGS, NOVEL PRODUCTS AND INTERMEDIATES THEREIN

This application is a division of application Ser. No. 381,113, now U.S. Pat. No. 4,467,103, filed May 24, 1982.

BACKGROUND OF THE INVENTION

1. Field of the Invention

The present invention relates to novel methods of preparing a wide variety of spectinomycin analogs and biologically acceptable salts thereof. Further, the invention relates both to novel intermediates and novel products therein. The novel products are spectinomycin analogs which can be used for the same biological purposes as spectinomycin. The processes of the invention provide for novel intermediates that are versatile and highly reactive exocyclic enones having formula I
  wherein $R_1$ and $R_2$ are blocking groups, and
  R is selected from the group consisting of hydrogen, alkyl of $C_1$ to $C_{20}$, inclusive, lower alkenyl, lower haloalkyl, lower aminoalkyl, lower alkynyl, and —$(CH_2)_n$—OX
  wherein X is selected from the group consisting of hydrogen, lower alkyl, lower alkenyl, benzyl, and acyl;
  n is an integer of from zero to four with the proviso that when n is zero —OX cannot be hydroxy.

Two methods are provided for the synthesis of the enones I by functionalization of the starting materials, i.e., protected spectinomycin and protected spectinomycin analogs having formula III'. Such functionalization provides for Mannich bases of formula III" either (1) directly or (2) through novel intermediate enamines having formula II. The Mannich bases give rise to the enones I. Finally, either the enones I or the enamines II are reacted with nucleophiles to obtain the wide variety of spectinomycin analogs including the novel products of the present invention.

$R_1$, $R_2$, and R in formulae I, II, III', and III" are as described above.

2. Description of the Art

Spectinomycin is a known antibiotic having the formula III. A microbiological preparation may be found in U.S. Pat. No. 3,234,092. A chemical synthesis including the nitrogen protected form, now among the starting materials of the present invention is disclosed in copending U.S. application Ser. No. 150,530, filed May 16, 1980, now U.S. Pat. No. 4,351,771. Numerous analogs of spectinomycin, including corresponding protected forms also among the present starting materials, are disclosed therein. Therefore, U.S. application Ser. No. 150,530 is incorporated herein by reference. Additional spectinomycin analogs are found in copending U.S. application Ser. No. 359,006, filed Mar. 17, 1982, now U.S. Pat. No. 4,420,624; U.S. application Ser. No. 020,073, filed Mar. 13, 1979, now U.S. Pat. No. 4,361,701; U.S. application Ser. No. 312,035, filed Oct. 16, 1981, now U.S. Pat. No. 4,405,797; U.S. application Ser. No. 068,926, filed Aug. 23, 1979, now U.S. Pat. No. 4,282,152; U.S. application Ser. No. 212,952, filed Dec. 4, 1980, now U.S. Pat. No. 4,337,347; U.S. application No. Ser. No. 212,950, filed Dec. 4, 1980, now U.S. Pat. No. 4,344,882; U.S. application No. Ser. No. 212,943, filed Dec. 4, 1980, now U.S. Pat. No. 4,345,086; U.S. application Ser. No. 285,164, filed July 20, 1981, now U.S. Pat. No. 4,380,651; U.S. application Ser. No. 285,165, filed July 20, 1981, now U.S. Pat. No. 4,380,652; U.S. application Ser. No. 358,957, filed Mar. 17, 1982, now U.S. Pat. No. 4,420,623; U.S. application Ser. No. 359,723, filed Mar. 19, 1982, now abandoned, and U.S. application Ser. No. 314,261, filed Oct. 23, 1981 now abandoned. However, none of these disclosures appreciate the novel processes, novel intermediates, or novel products of the present invention.

In general, preparation of Mannich bases are well known. Representative references of such preparations are March, "The Mannich Reaction", *Advanced Organic Chemistry: Reactions, Mechanisms and Structure*, pp. 670–672, McGraw-Hill Book Company (1968); Flick, "The Use of a Mannich Base as a Source of an Unsaturated Ketone for Condensations With an Active Methylene Compound", *Organic Reactions*, vol. 1, pp. 320–322, New York: John Wiley and Sons, Inc. (1942); Brewster et al. "Alkylations With Tertiary Amines", *Organic Reactions*, vol. 7, pp. 126–130, New York: John Wiley and Sons, Inc. (1953); Bergman et al. "Robinson's Modification of the Michael Condensation", *Organic Reactions*, vol. 10, pp. 222–223: New York, John Wiley and Sons, Inc. (1959). However, none of these references makes obvious the present invention.

SUMMARY OF THE INVENTION

The present invention includes novel compounds having the formula
  wherein R, $R_1$ and $R_2$ are as defined above;

The present invention also includes novel compounds having the formula II wherein $R_1$, $R_2$, and R are as defined above.

Finally, the present invention includes novel compounds having the formula V
  wherein $R_3$ and $R_4$ are the same and are hydrogen or blocking groups;
  R is defined as above, and
  —T is selected from the group consisting of —OY, —$CHR_5C(O)R_6$, —$NH_2$, —$NHR_5$, —$NR_5R_6$, —$NO_2$, —$NHNH_2$, —$N_3$, —$NR_5SO_2R_6$, —SH, —$SR_5$, —S—S—, —$CH[C(O)R_5][C(O)R_6]$, —$C\equiv N$, —$CH(CN)R_5$, —$CH[C(O)R_5][C(O)OR_6]$, —$CH[C(O)OR_5][C(O)OR_6]$, —$CR_5R_6NO_2$, —$CR_5R_6SO_2R_7$, —$CR_5C(N)C(N)$
  wherein Y is aryl, —$CR_5=CHR_6$ or —N=O, and
  $R_5$, $R_6$, and $R_7$ are the same or different and are lower alkyl or aryl and biologically acceptable salts thereof.

In the foregoing designation of variables alkyl of $C_1$ to $C_{20}$ means methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, and isomers thereof. This designation is meant to include the preferred alkyl group, straight, cyclic or branch chain system in which the longest extension of the cyclic or branch chain system contains from 1 to 5 carbon atoms, inclusive.

Lower alkyl, —$(CH_2)n$— wherein n is an integer of zero through four, and alkyl as is found in the terms lower haloalkyl or lower aminoalkyl means an alkyl of from one through four carbon atoms, for example, methyl, ethyl, propyl, isopropyl, butyl, sec-butyl, isobutyl, and tert-butyl.

Halo means fluoro, chloro, bromo or iodo.

Lower alkenyl means ethylidene, propylidene, butylidene, pentylidene, hexylidene, heptylidene, octylidene and the isomeric forms thereof.

Lower alkynyl means ethynyl, propynyl, butynyl, pentynyl, hexynyl, heptynyl, octynyl and the isomeric forms thereof.

Acyl means formyl, acetyl, propionyl, butyryl, pentanoyl and isomeric forms thereof.

Blocking groups mean aralkoxycarbonyl, halogenated alkoxy carbonyl, and alkoxy carbonyl, such as, for example, 4-methoxy benzyloxycarbonyl, benzyloxycarbonyl, isopropoxycarbonyl, isobutyloxycarbonyl, cyclopentyloxycarbonyl, cyclohexyloxycarbonyl, $\beta,\beta,\beta$-trichloroethoxycarbonyl, or tertiary-butoxycarbonyl, preferably either benzoxycarbonyl or tertiary butoxycarbonyl.

Another aspect of the present invention is a process for preparing compounds having the formula IV
wherein $R_3$ and $R_4$ are the same and are hydrogen or blocking groups;
R is as defined above, and
Q is a nucleophile which comprises
(1) contacting the compound III' with N,N-dimethyl-(methylene)ammonium chloride, that is, $CH_2=N(CH_3)_2Cl$ and trifluoroacetic acid (TFA) in acetonitrile ($CH_3CN$) to obtain compound III'';
(2) enolization of compound III'' to obtain enone I;
(3) contacting the product of steps 1 or 2 with a nucleophile and triethylamine ($Et_3N$) to obtain the compound IVa and then, if desired;
(4) further treating IVa to obtain IVb A preferred embodiment of the nucleophile —Q comprises —OZ, —(CH$_2$)$_b$OZ, —CHR$_5$C(O)R$_6$, —NH$_2$, —NHR$_5$, —NR$_5$R$_6$, —NO$_2$, —NHNH$_2$, —N$_3$, —NR$_5$SO$_2$R$_6$, —SH, —SR$_5$, —S—S—, —C≡CR$_5$, —CH[C(O)R$_5$][C(O)R$_6$], —C≡N, —CHCNR$_5$, —CH[C(O)R$_5$][C(O)OR$_6$], —CH[C(O)OR$_5$][C(O)OR$_6$], —CR$_5$R$_6$NO$_2$, —CR$_5$R$_6$SO$_2$R$_7$, —CR$_5$(CN)$_2$, hydrogen, lower alkyl, lower alkenyl, lower haloalkyl, lower aminoalkyl, or lower alkynyl
wherein Z is hydrogen, aryl, —N=O, lower alkyl, lower alkenyl, benzyl or acyl;
b is an integer of one through eight;
$R_1$, $R_2$, R and $R_3$ through $R_7$ are all as defined above (see Scheme A).

The above process may be carried out without separately conducting steps 1 and 2 above which identifies compound III'' and the enone I. Thus, the product of step 1 may be contacted with the nucleophile and $Et_3N$ to obtain the desired compound IVa (see Scheme D).

The present invention includes an alternate process for the preparation of compounds having the formula IVa
wherein $R_1$, $R_2$, R, and Q are all as defined above which comprises
(1) contacting the compound III' with N,N-dimethylformamide-ditertiary-butyl acetal and trifluoroacetic acid in dimethylformamide (TFA/DMF) to obtain compounds having the formula II;
(2) contacting the product of step 1 with sodium cyanoborohydride ($NaCNBH_3$) in methanol at about pH 4 to provide compound III'';
(3) enolization of compound III'' to obtain compound I;
(4) contacting the product of steps 2 or 3 with a nucleophile in the presence of triethylamine ($Et_3N$) to obtain compound IVa (see Scheme B).

Finally, the present invention includes the processes for the preparation of compounds having the formula IVa
wherein $R_1$, $R_2$, R, and Q are all as defined above which comprises (1) contacting the compound III' with N,N-dimethylformamide-ditertiary-butyl acetal and trifluoro acetic acid and dimethylformamide to obtain the compound II;
(2) contacting the product of step 1 with sodium cyanoborohydride in methanol at pH 4 and treating the mixture with the nucleophile and triethylamine to give the compound IVa (see Scheme C).

The compound IVa prepared in the final step of each of the above alternate processes may also be further deprotected to obtain the desired spectinomycin analogs IVb. Deprotection may be accomplished by known methods in the art or by contacting the compound IVa with thioanisole (phenyl $SCH_3$/TFA in neat trifluoroacetic acid). See step 4 in Scheme A, step 5 in Scheme B, and step 3 in Schemes C and D.

Spectinomycin analogs of this invention are meant to include biologically acceptable acid addition salts.

Biologically acceptable acid addition salts of the invention compounds and the compounds prepared by the invention processes can be made by neutralizing the compounds with an appropriate acid to below about pH 7.0 and advantageously to about from pH 2 to about pH 6. Suitable acids for this purpose include tartaric, gluconic, lactic, hydrochloric, sulfuric, phosphoric, sulfamic, hydrobromic and the like. Acid salts of spectinomycin analogs can be used for the same biological purposes as the parent compound.

The term "nucleophile" is meant to be nonlimiting, and the skilled artisan can readily determine operable groups from a broad range of possible reacting groups in the art known for the presence thereon of an unshared pair of electrons, and therefore, are included in the term "nucleophile." See March, *Advanced Organic Chemistry: Reactions, Mechanisms, and Structure* pp. 199–200 and pp. 287–290, McGraw-Hill Book Co. (1968) and Cram et al. *Organic Chemistry*, pp. 272–275, McGraw-Hill Book Co. Preferred nucleophiles for use in the processes of this invention comprise HOM$_1$, R$_5$OH, R$_5$OM$_1$, R$_5$CH=C(OM$_1$)R$_6$, NH$_3$, R$_5$NH$_2$, R$_5$R$_6$NH, NO$_2$M$_1$, NH$_2$NH$_2$, N$_3$M$_1$, R$_5$SO$_2$NR$_6$M$_1$, H$_2$S, HSM$_1$, R$_5$SH, S$_2$M$_2$, R$_5$M$_1$, R$_5$C≡CM$_1$, R$_5$C(O)CHC(O)R$_6$M$_1$⇌R$_5$C(OM$_1$)=CH(O)R$_6$⇌R$_5$C(O)CH=C(OM$_1$)R$_6$, M$_1$C≡N, R$_5$CHC≡N, RSM$_1$, R$_5$C(O)CHC(O)OR$_6$M$_1$, R$_5$OC(O)CHC(O)OR$_6$M$_1$, R$_5$R$_6$C(M$_1$)NO$_2$, R$_5$R$_6$C(M$_1$)SO$_2$R$_7$ or HC(R$_5$)(C≡N)(C≡N), HR$_8$ or M$_1$R$_8$
wherein $R_5$, $R_6$, and $R_7$ are the same or different and are lower alkyl or aryl; $R_8$ is lower alkyl, lower alkenyl, lower haloalkyl, lower aminoalkyl or lower alkynyl;
$M_1$ is a monovalent metal or ion, and
$M_2$ is a divalent metal.

Aryl with respect to the present invention includes phenyl and phenyl substituted with, for example, 1 to 2 alkyl, alkoxy, or alkylthio such as methylthio so that the named moiety is a substantially hydrocarbyl moiety.

The monovalent metal denoted $M_1$ herein is $Na^+$, $K^+$, or $Li^+$.

The divalent metal denoted $M_2$ herein is $Mg^{++}$, $Ca^{++}$, or $Ba^{++}$.

DETAILED DESCRIPTION OF THE INVENTION

The functionalization of the compound III' with N,N-dimethyl-(methylene)ammonium chloride to obtain compound III'' shown as step 1 in Scheme A occurs in a solution of acetonitrile or similar solvents such as tetrahydrofuran, or 1,2-dimethoxyethane in the presence of trifluoroacetic acid. The reaction is most efficaciously run at a temperature of 20° to 70° with molar ratios of compound III' to N,N-dimethyl(methylene)ammonium chloride to trifluoroacetic acid in the ranges from 8:10:3 to 8:30:10. Preferably, reaction conditions are at a temperature of 35° C. to 45° C. using acetonitrile as a solvent with the ratio of compound III' to N,N-dimethyl(methylene)ammonium chloride and trifluoroacetic acid from 8:20:6 to 8:25:10.

A major competing side reaction at elevated temperatures occurs following the beta elimination shown in step 2 of Scheme A and step 3 of Scheme B to give the enone I. The side reaction is subsequently dimerized to a product having formula VII and formula VIII shown in step 3 of Scheme A and step 4 shown in Scheme B. However, the product III'' can be obtained free of any residual starting material, enone or dimer by simply partitioning of the crude product mixture between ethyl acetate and dilute aqueous acid, such as, HCl, $H_2SO_4$, or HBr. The aqueous layer is lyophilized to give the compound III'' which is extremely hygroscopic but stable at 25° C.

Generally, the functionalization of N,N'-protected compound III' to obtain compound III'' may also be accomplished by the preparation of an enamine II as shown in steps 1 of Scheme B and Scheme C. This functionalization is accomplished by using N,N-dimethylformamide-ditertiary-butylacetal and trifluoroacetic acid in dimethylformamide as shown in step 1 of Scheme B. A solution of III' in dimethylformamide is cooled to about 0° C. to which is added the N,N-dimethylformamide-di-tert-butylacetal and trifluoroacetic acid. The reaction mixture is allowed to warm and reaction proceeds smoothly at from 15° C. to 35° C., preferably about 25° C. Other reagents such as N,Ndimethylformamide-dimethylacetal in aprotic solvents such as acetonitrile or dimethylformamide may be used as shown in step 1 of Scheme C. However, N,N-dimethylformamide-dimethylacetal gives only low yields of the desired enamines. Thus, care must be taken to avoid obtaining the rearranged compound N,N'protected actinospectinoic acid methylester or analogs thereof having the formula VI. The enamine II is then reduced with sodium cyanoborohydride in methanol at a pH from 3.5 to 6, preferably about pH 4 to obtain the N,N'-diprotected-4'-(dimethylaminomethyl)compound as a hydrochloride salt III'' as shown in step 2 of both Scheme B and Scheme C. Maintenance of the acidic pH during reduction is critical for obtaining the product III'' of this step. It is extracted with dilute base, such as $NaHCO_3$.

On the other hand, it appears that the trifluoroacetic acid catalyzes the functionalization reaction of step 1 in each of the schemes shown by enolyzing the carbonyl of the protected starting material III'. It is believed that such enolization occurs to the carbonyl containing compound III'', thus providing a route for $\beta$ elimination and subsequent reaction with the nucleophile shown in each of the Schemes A through D. Although, the enone I wherein R is methyl of the following examples is not isolated, evidence of its existence may be found in fractions obtained from chromatography of the reaction mixtures described above for obtaining compounds III''. Attempts to concentrate these fractions produce a dimer having the formulae VII and VIII shown in Schemes A and B. The dimeric structure of compound VII and compound VIII, homogeneous by TLC, is evidenced by the number of signals in the CMR and off resonance decoupling experiments.

Since the enone, free of solvent, is not isolated in the present invention it is shown in brackets in Scheme A and Scheme B. Thus, the pH of the reaction product mixture obtained in step 1 of Scheme A and step 2 of Scheme B described above is raised from pH of 7 to pH of 9, preferably from between pH 7.5 to pH 8.0 with triethylamine in the presence of a nucleophile to obtain the product IVa. The reaction with the nucleophile is conducted at from −50° C. to 40° C., preferably 25° C. for about 3 hours, preferably from two to four hours.

A one pot procedure as shown by step 2 of Scheme C may be more efficacious. In the one pot reaction a solution of the enamine II obtained by the above described procedure is dissolved in a lower alcohol, such as ethanol, propanol, or methanol at a pH of from 3 to 5, preferably about pH 4. A solution of sodium cyanoborohydride in methanol is added to the enamine solution while maintaining the pH at about four with methanolic hydrogen chloride. When the reaction mixture contains only the amine III'' and enone I as shown by thin layer chromatography the reaction is complete. The nucleophile and triethylamine are added and the reaction is stirred for 3 hours at 25° C.

Likewise, a one pot reaction as shown in Scheme D may be more efficacious to accomplish the reation as previously described as steps of Scheme A. In this reaction the conditions are as described for steps 1 and 3 of Scheme A above with the added advantage that intermediates III'' and I are not necessarily isolated or identified.

Finally, in step 4 of Scheme A, step 5 of Scheme B, step 3 of Scheme C, and step 3 of Scheme D the compound IVa is deprotected to obtain the desired active compound IVb. Deprotection means removing the blocking groups from the nitrogen in the actinamine ring of IVa and replacing them with hydrogen. The particular conditions of the deprotection step depend upon the particular oxy groups, that is, group $R_1$ or $R_2$ that block the nitrogen on the actinamine ring. Further, the R substituent as well as the nucleophile added by the present invention process to prepare compounds IVa determine the particular conditions for the deprotection step described here. Many conventional methods may be used as previously described in U.S. application Ser. No. 020,073, filed Nov. 23, 1979, (Case 3589) if appropriate. However, since the nucleophile may poison the catalyst in attempts to deprotect the compound IVa then deprotection may be accomplished using thioanisole in neat trifluoroacetic acid. This is preferred.

Preferred compounds of the present invention are those wherein R is an alkyl group, straight, cyclic or branch chain system, in which the longest extension of the cyclic or branch chain system contains from 1 to 5 carbon atoms, inclusive. Such an R substituent is as disclosed in U.S. application Ser. No. 359,723, filed Mar. 19, 1982 (Case 4034) and, therefore, is incorporated by reference. Most preferred are those wherein R is n-butyl, n-pentyl or n-hexyl.

The following examples are indicative of the present invention and are not to be construed as limiting. Those skilled in the art will readily recognize the appropriate variations from the procedure both as to variations on the starting material III' as well as reaction conditions and techniques. These examples indicate the best mode presently known to the inventor. In each ml is milliliters; g is grams; mMol is millimole; C. is degrees centigrade; ppm is parts per million.

EXAMPLE I

Preparation of N,N'-dicarbobenzyloxy-4'-(dimethylaminomethyl)-spectinomycin (III" wherein $R_1$ and $R_2$ are the same and are carbobenzyloxy, and R is methyl). See Scheme A step 1.

A solution of distilled acetyl chloride (1.50 ml, 1.58 g, 20.0 mMol) in ether (5 ml) is added carefully to a solution of N,N,N',N'-tetramethyldiaminomethane (2.70 ml, 2.02 g, 19.8 mMol) in ether (50 ml). At 25° C. under $N_2$ atmosphere $CH_2=N(CH_3)Cl$ precipitates out immediately as a white solid. After 30 minutes the solvent is removed with a filter stick, and the solid is washed two times with 25 milliliters of ether. A CMR of a solid prepared by this procedure showed (d3-acetonitrile) 79.4, 38.8 ppm.

To this pre-formed reagent is added N,N'-dicarbobenzyloxyspectinomycin (III' wherein $R_1$ and $R_2$ are carbobenzyloxy, and R is methyl) (5.0 g, 8.3 mMol), acetonitrile (25 ml), and trifluoroacetic acid (0.5 ml, 0.74 g, 6.5 mMol). The substrate and reagent are stirred at 25° C. until a solution is effected. The reaction temperature is then raised to 40° C. and kept at 40° C. for a period of 72 hours. The reaction is concentrated at 45° C. and the crude solid product is redissolved in 150 ml of 0.05N hydrogen chloride and 150 ml of ethyl acetate. The layers are separated, and the organic layer is reextracted with 75 ml of the acid. Th aqueous fractions are combined, and the excess acid and dissolved ethyl acetate are removed on the rotary evaporator at 45° using a nitrogen stream. The sample is frozen and lyophilized to give 6 g of the crude product N,N'-dicarbobenzyloxy-4'-(dimethylaminomethyl)-spectinomycin (III" wherein $R_1$ and $R_2$ are carbobenzyloxy, and R is methyl). It is kept under nitrogen in a dry box.

The product prepared by the above description shows the following CMR (d3-acetonitrile) 157.7, 138.5, 129.7, 129.0, 128.8, 95.4, 91.4, 74.5, 74.0, 69.6, 67.9, 66.5, 66.2, 60.8, 57.6, 51.2, 47.0, 35.5, 32.5, 18.2 ppm.

Following the procedure in Example I, but substituting the appropriate N,N'-dicarbobenzyloxy spectinomycin (III' wherein $R_1$ and $R_2$ are carbobenzyloxy, and R is selected from the group as defined above) the following N,N'-dicarbobenzyloxy-4'-(dimethylaminomethyl)-spectinomycin derivative III" can be prepared.

1. N,N'-dicarbobenzyloxy-4'-(dimethylaminomethyl)-5'-demethylspectinomycin (III" wherein $R_1$ and $R_2$ are carbobenzyloxy, and R is hydrogen);
2. N,N'-dicarbobenzyloxy-4'-(dimethylaminomethyl)-6'-hydroxyspectinomycin (III" wherein $R_1$ and $R_2$ are carbobenzyloxy, and R is hydroxymethyl);
3. N,N'-dicarbobenzyloxy-4'-(dimethylaminomethyl)-6'-chlorospectinomycin (III" wherein $R_1$ and $R_2$ are carbobenzyloxy, and R is chloromethyl);
4. N,N'-dicarbobenzyloxy-4'-(dimethylaminomethyl)-6'-bromospectinomycin) (III" wherein $R_1$ and $R_2$ are carbobenzyloxy, and R is bromomethyl);
5. N,N'-dicarbobenzyloxy-4'-(dimethylaminomethyl)-6'-n-butylspectinomycin (III" wherein $R_1$ and $R_2$ are carbobenzyloxy, and R is pentyl);
6. N,N'-dicarbobenzyloxy-4'-(dimethylaminomethyl)-6'-acetoxyspectinomycin (III" wherein $R_1$ and $R_2$ are carbobenzyloxy, and R is acetoxymethyl);
7. N,N'-dicarbobenzyloxy-4'-(dimethylaminomethyl)-6'-phenylmethoxyspectinomycin (III" wherein $R_1$ and $R_2$ are carbobenzyloxy, and R is phenylmethoxymethyl);
8. N,N'-dicarbobenzyloxy-4'-(dimethylaminomethyl)-5'-demethyl-5'-phenylmethoxyspectinomycin (III" wherein $R_1$ and $R_2$ are carbobenzyloxy, and R is phenylmethoxy);
9. N,N'-dicarbobenzyloxy-4'-(dimethylaminomethyl)-5'-demethyl-5'-methoxyspectinomycin (III" wherein $R_1$ and $R_2$ are carbobenzyloxy, and R is methoxy);
10. N,N'-dicarbobenzyloxy-4'-(dimethylaminomethyl)-6'-methylspectinomycin (III" wherein $R_1$ and $R_2$ are carbobenzyloxy, and R is ethyl);
11. N,N'-dicarbobenzyloxy-4'-(dimethylaminomethyl)-6'-methoxyspectinomycin (III" wherein $R_1$ and $R_2$ are carbobenzyloxy, and R is methoxymethyl);
12. N,N'-dicarbobenzyloxy-4'-(dimethylaminomethyl)-6'-aminospectinomycin (III" wherein $R_1$ and $R_2$ are carbobenzyloxy, and R is aminomethyl);
13. N,N'-dicarbobenzyloxy-4'-(dimethylaminomethyl)-6'-ethylspectinomycin (III" wherein $R_1$ and $R_2$ are carbobenzyloxy, and R is propyl);
14. N,N'-dicarbobenzyloxy-4'-(dimethylaminomethyl)-6'-n-pentylspectinomycin (III" wherein $R_1$ and $R_2$ are carbobenzyloxy, and R is n-hexyl);
15. N,N'-dicarbobenzyloxy-4'-(dimethylaminomethyl)-5'-dimethyl-5'-methylethynyldemethylspectinomycin (III" wherein $R_1$ and $R_2$ are carbobenzyloxy, and R is methylethynyl);
16. N,N'-dicarbobenzyloxy-4'-(dimethylaminomethyl)-6'-n-propylspectinomycin (III" wherein $R_1$ and $R_2$ are carbobenzyloxy, and R is n-butyl);
17. N,N'-dicarbobenzyloxy-4'-(dimethylaminomethyl)-6'-ethenyloxymethylspectinomycin (III" wherein $R_1$ and $R_2$ are carbobenzyloxy, and R is ethenyloxyethyl);

EXAMPLE II

Preparation of 4'-Enamine, N,N'-dicarbobenzyloxy-4'-dimethylaminomethylenespectinomycin (II wherein $R_1$ and $R_2$ are carbobenzyloxy, and R is methyl). See Scheme B step 1 or Scheme C step 1.

To a solution of N,N'-dicarbobenzyloxyspectinomycin (III' wherein $R_1$ and $R_2$ are carbobenzyloxy, and R is methyl) (5.0 g, 8.33 mMol) in dimethylformamide (10 ml) cooled to 0° C. is added N,N-dimethylformamide-di-tert-butyl-acetal (9 ml, 7.6 g, 37.6 mMol) and trifluoroacetic acid (0.9 ml, 1.35 g, 11.8 mMol). The reaction is cooled an additional 15 minutes then allowed to warm to 25° C. The reaction is nearly complete after seven hours. It is stoppered and stored at $-5°$ C. for two days. The solution is then concentrated at 45° C. to an oily solid. The crude product is then chromatographed on 250 g of silica gel (E. Merck Silica Gel 60) using medium pressure and a gradient elution from 1:9 to 1:1 acetone:chloroform. The 4'-enamine,N-N'-dicarbobenzyloxy-4'-dimethylaminomethylenespectinomycin, prepared by this method (II, wherein $R_1$ and $R_2$ are carbobenzyloxy, and R is methyl) (2.1 g, 38.7%) was isolated as an orange colored solid and characterized as follows:

High Resolution Mass Spec.: (Tri-TMS) calcd for $C_{42}H_{65}N_3O_{11}Si_3=871.3927$, Found: 871.3955. CMR (d6-Acetone): 186.7, 157 (m), 154.6, 138.1, 128.4, 129.1, 102.9, 95.0, 89.5, 74.7, 74.1, 69.5, 67.2, 66.5, 65.5, 60 (m), 57.0 (m), 31.6, 25.2 ppm. PMR (CDCl3): δ 1.4 (CH3, d), 3.0 (NCH3, s), 3.7–4.8 (m), 5.0 (—CH2—o, s), 7.3 (ArH, s).

IR (Mull) 3400 s (OH), 1690 s (C=O), 1585, 1555 s, 1495 (C=C), 1420, 1345, 1300, 1165, 1080, 1060, 770, 740, 695 cm$^{-1}$.

CD (MeOH) $[\theta]_{343}$ $_{nm}{}^{max}=-9,200\pm1,100$; $[\theta]_{274}$ $_{nm}{}^{max}=+4,600\pm1,100$ CD (CH$_3$CN) $[\theta]_{346}$ $_{nm}{}^{max}=-11,500\pm1,000$ $[\alpha]D$ (CHCl$_3$, C=0.483)=$-9°$; UV (CH$_3$CN) 204 sh ($\epsilon$=22,750) 334 ($\epsilon$=13,950).

Following the procedure in Example II but substituting the appropriately substituted N,N'-dicarbobenzyloxyspectinomycin (III' wherein R$_1$ and R$_2$ are carbobenzyloxy, and R is selected from the group defined above) the following novel 4'-enamine is prepared.

1. N,N'-dicarbobenzyloxy-4'-dimethylaminomethylene-5'-demethylspectinomycin (II wherein R$_1$ and R$_2$ are carbobenzyloxy, and R is hydrogen);
2. N,N'-dicarbobenzyloxy-4'-dimethylaminomethylene-6'-hydroxyspectinomycin (II wherein R$_1$ and R$_2$ are carbobenzyloxy, and R is hydroxymethyl);
3. N,N'-dicarbobenzyloxy-4'-dimethylaminomethylene-6'-chlorospectinomycin (II wherein R$_1$ and R$_2$ are carbobenzyloxy, and R is chloromethyl);
4. N,N'-dicarbobenzyloxy-4'-dimethylaminomethylene-6'-bromospectinomycin (II wherein R$_1$ and R$_2$ are carbobenzyloxy, and R is bromomethyl);
5. N,N'-dicarbobenzyloxy-4'-dimethylaminomethylene-6'-n-butylspectinomycin (II wherein R$_1$ and R$_2$ are carbobenzyloxy, and R is pentyl);
6. N,N'-dicarbobenzyloxy-4'-dimethylaminomethylene-6'-acetoxyspectinomycin (II wherein R$_1$ and R$_2$ are carbobenzyloxy, and R is acetoxymethyl);
7. N,N'-dicarbobenzyloxy-4'-dimethylaminomethylene-6'-phenylmethoxyspectinomycin (II wherein R$_1$ and R$_2$ are carbobenzyloxy, and R is phenylmethoxymethyl);
8. N,N'-dicarbobenzyloxy-4'-dimethylaminomethylene-5'-demethyl-5'-phenylmethoxyspectinomycin (II wherein R$_1$ and R$_2$ are carbobenzyloxy, and R is phenylmethoxy);
9. N,N'-dicarbobenzyloxy-4'-dimethylaminomethylene-5'-demethyl-5'-methoxyspectinomycin (II wherein R$_1$ and R$_2$ are carbobenzyloxy, and R is methoxy);
10. N,N'-dicarbobenzyloxy-4'-dimethylaminomethylene-6'-methylspectinomycin (II wherein R$_1$ and R$_2$ are carbobenzyloxy, and R is ethyl);
11. N,N'-dicarbobenzyloxy-4'-dimethylaminomethylene-6'-methoxyspectinomycin (II wherein R$_1$ and R$_2$ are carbobenzyloxy, and R is methoxymethyl);
12. N,N'-dicarbobenzyloxy-4'-dimethylaminomethylene-6'-aminospectinomycin (II wherein R$_1$ and R$_2$ are carbobenzyloxy, and R is aminomethyl);
13. N,N'-dicarbobenzyloxy-4'-dimethylaminomethylene-6'-ethylspectinomycin (II wherein R$_1$ and R$_2$ are carbobenzyloxy, and R is propyl);
14. N,N'-dicarbobenzyloxy-4'-dimethylaminomethylene-6'-n-pentylspectinomycin (II wherein R$_1$ and R$_2$ are carbobenzyloxy, and R is n-hexyl);
15. N,N'-dicarbobenzyloxy-4'-dimethylaminomethylene-5'-demethyl-5'-methylethynylspectinomycin (II wherein R$_1$ and R$_2$ are carbobenzyloxy, and R is methylethynyl);
16. N,N'-dicarbobenzyloxy-4'-dimethylaminomethylene-6'-n-propylspectinomycin (II wherein R$_1$ and R$_2$ are carbobenzyloxy, and R is n-butyl);
17. N,N'-dicarbobenzyloxy-4'-dimethylaminomethylene-6'-ethenyloxymethylspectinomycin (II wherein R$_1$ and R$_2$ are carbobenzyloxy, and R is ethenyloxyethyl);

EXAMPLE III

Preparation of N,N'-dicarbobenzyloxy-4'-(dimethylaminomethyl)-spectinomycin hydrogen chloride (III'' wherein R$_1$ and R$_2$ are carbobenzyloxy, and R is methyl), 4'-enone (I, wherein R$_1$ and R$_2$ are carbobenzyloxy, and R is methyl) and dimer (VII and VIII wherein R$_1$ and R$_2$ are carbobenzyloxy). See Scheme B steps 2, 3, and 4.

To a solution of the 4'-enamine, N,N'-dicarbobenzyloxy-4'-dimethylaminomethylenespectinomycin, from Example II above (414 mg, 0.63 mMol) in methanol (5 ml) at pH 4 is added sodium cyanoborohydride (13.2 mg, 0.21 mMol) over a period of 10 minutes. The pH of the solution is readjusted after each addition of hydride with methanolic hydrogen chloride using methyl orange as an indicator. The reaction is stirred at 25° C. for two hours then concentrated to give the crude product mixture. Two major product spots are observed by TLC in 1:9 MeOH:CHCl$_3$, the 4'-enone, N,N'-dicarbobenzyloxy-4'-methylenespectinomycin, (I wherein R$_1$ and R$_2$ are carbobenzyloxy, and R is methyl) is less polar (Rf 0.6) than the starting material 4'-enamine, N,N'-dicarbobenzyloxy-4'-dimethylaminomethylenespectinomycin, (Rf 0.5) with intense UV and permanganate activity, and the amine, N,N'-di-carbobenzyloxy-4'-(dimethylaminomethyl)-spectinomycin hydrogen chloride (III'' wherein R$_1$ and R$_2$ are carbobenzyloxy, and R is methyl) which remains at the origin. The crude product mixture is redissolved in chloroform (60 ml), extracted with 0.05M NaOH (10 ml) and water (20 ml) then dried over Na$_2$SO$_4$ and concentrated to give 375 mg of the dimer (VII and VIII wherein R$_1$ and R$_2$ are carbobenzyloxy). The sample is chromatographed on silica gel 60 (40 g) using 2 percent MeOH:CHCl$_3$. Fractions containing the pure 4'-enone, N,N'-dicarbobenzyloxy-4'-methylenespectinomycin, (I wherein R$_1$ and R$_2$ are carbobenzyloxy, and R is methyl) are pooled to give 100 mg of material. TLC of this pooled fraction shows that the 4'-enone is converted in part to the more polar spot dimer. Almost complete conversion to the dimer was observed when a 4'-enone prepared by this method was allowed to stand in solution.

It showed a CMR (d$_6$-acetone): 193.3, 157.8, 157.0, 143.1, 138.2, 129.2, 128.4, 111.2, 97.6, 95.9, 93.8, 88.7, 82.7, 75.2, 74.5, 72.4, 71.2, 67.2, 66.8, 65.1, 31.5, 22.5, 20.0, 17.7, 14.1 ppm.

Following the procedure in Example III but substituting the appropriate N,N'-dicarbobenzyloxy-4'-dimethylaminomethylenespectinomycin (II wherein R$_1$ and R$_2$ are carbobenzyloxy, and R is selected from the group as defined above) the following 4'-enone is prepared.

1. N,N'-dicarbobenzyloxy-4'-methylene-5'-demethylspectinomycin (I wherein R$_1$ and R$_2$ are carbobenzyloxy, and R is hydrogen);
2. N,N'-dicarbobenzyloxy-4'-methylene-6'-hydroxyspectinomycin (I wherein R$_1$ and R$_2$ are carbobenzyloxy, and R is hydroxymethyl);
3. N,N'-dicarbobenzyloxy-4'-methylene-6'-chlorospectinomycin (I wherein R$_1$ and R$_2$ are carbobenzyloxy, and R is chloromethyl);
4. N,N'-dicarbobenzyloxy-4'-methylene-6'-bromospectinomycin (I wherein R$_1$ and R$_2$ are carbobenzyloxy, and R is bromomethyl);

5. N,N'-dicarbobenzyloxy-4'-methylene-6'-n-butylspectinomycin (I wherein R$_1$ and R$_2$ are carbobenzyloxy, and R is pentyl);
6. N,N'-dicarbobenzyloxy-4'-methylene-6'-acetoxyspectinomycin (I wherein R$_1$ and R$_2$ are carbobenzyloxy, and R is acetoxymethyl);
7. N,N'-dicarbobenzyloxy-4'-methylene-6'-phenylmethoxyspectinomycin (I wherein R$_1$ and R$_2$ are carbobenzyloxy, and R is phenylmethoxymethyl);
8. N,N'-dicarbobenzyloxy-4'-methylene-5'-demethyl-5'-phenylmethoxyspectinomycin (I wherein R$_1$ and R$_2$ are carbobenzyloxy, and R is phenylmethoxy);
9. N,N'-dicarbobenzyloxy-4'-methylene-5'-demethyl-5'-methoxyspectinomycin (I wherein R$_1$ and R$_2$ are carbobenzyloxy, and R is methoxy);
10. N,N'-dicarbobenzyloxy-4'-methylene-5'-demethyl-6'-methylspectinomycin (I wherein R$_1$ and R$_2$ are carbobenzyloxy, and R is ethyl);
11. N,N'-dicarbobenzyloxy-4'-methylene-5'-demethyl-6'-methoxyspectinomycin (I wherein R$_1$ and R$_2$ are carbobenzyloxy, and R is methoxy);
12. N,N'-dicarbobenzyloxy-4'-methylene-6'-aminospectinomycin (I wherein R$_1$ and R$_2$ are carbobenzyloxy, and R is aminomethyl);
13. N,N'-dicarbobenzyloxy-4'-methylene-6'-ethylspectinomycin (I wherein R$_1$ and R$_2$ are carbobenzyloxy, and R is propyl);
14. N,N'-dicarbobenzyloxy-4'-methylene-6'-n-pentylspectinomycin (I wherein R$_1$ and R$_2$ are carbobenzyloxy, and R is n-hexyl);
15. N,N'-dicarbobenzyloxy-4'-methylene-5'-demethyl-5'-methylethynylspectinomycin-4'-yl enone (I wherein R$_1$ and R$_2$ are carbobenzyloxy, and R is methylethynyl);
16. N,N'-dicarbobenzyloxy-4'-methylene-6'-n-propylspectinomycin (I wherein R$_1$ and R$_2$ are carbobenzyloxy, and R is n-butyl);
17. N,N'-dicarbobenzyloxy-4'-methylene-6'-ethenyloxymethylspectinomycin (I wherein R$_1$ and R$_2$ are carbobenzyloxy, and R is ethenyloxyethyl);

Likewise the procedure in Example III having the appropriately substituted enamine for preparing the 4'-enone is then also converted to the following novel dimers:

1. Formula VII wherein R$_1$ and R$_2$ are carbobenzyloxy, and R is hydrogen;
2. Formula VIII wherein R$_1$ and R$_2$ are carbobenzyloxy, and R is hydrogen;
3. Formula VII wherein R$_1$ and R$_2$ are carbobenzyloxy, and R is hydroxymethyl;
4. Formula VIII wherein R$_1$ and R$_2$ are carbobenzyloxy, and R is hydroxymethyl;
5. Formula VII wherein R$_1$ and R$_2$ are carbobenzyloxy, and R is chloromethyl;
6. Formula VIII wherein R$_1$ and R$_2$ are carbobenzyloxy, and R is chloromethyl;
7. Formula VII wherein R$_1$ and R$_2$ are carbobenzyloxy, and R is bromomethyl;
8. Formula VIII wherein R$_1$ and R$_2$ are carbobenzyloxy, and R is bromomethyl;
9. Formula VII wherein R$_1$ and R$_2$ are carbobenzyloxy, and R is pentyl;
10. Formula VIII wherein R$_1$ and R$_2$ are carbobenzyloxy, and R is pentyl;
11. Formula VII wherein R$_1$ and R$_2$ are carbobenzyloxy, and R is acetoxymethyl;
12. Formula VIII wherein R$_1$ and R$_2$ are carbobenzyloxy, and R is acetoxymethyl;
13. Formula VII wherein R$_1$ and R$_2$ are carbobenzyloxy, and R is phenylmethoxymethyl;
14. Formula VIII wherein R$_1$ and R$_2$ are carbobenzyloxy, and R is phenylmethoxymethyl;
15. Formula VII wherein R$_1$ and R$_2$ are carbobenzyloxy, and R is phenylmethoxy;
16. Formula VIII wherein R$_1$ and R$_2$ are carbobenzyloxy, and R is phenylmethoxy;
17. Formula VII wherein R$_1$ and R$_2$ are carbobenzyloxy, and R is methoxy;
18. Formula VIII wherein R$_1$ and R$_2$ are carbobenzyloxy, and R is methoxy;
19. Formula VII wherein R$_1$ and R$_2$ are carbobenzyloxy, and R is ethyl;
20. Formula VIII wherein R$_1$ and R$_2$ are carbobenzyloxy, and R is ethyl;
21. Formula VII wherein R$_1$ and R$_2$ are carbobenzyloxy, and R is methoxymethyl;
22. Formula VIII wherein R$_1$ and R$_2$ are carbobenzyloxy, and R is methoxymethyl;
23. Formula VII wherein R$_1$ and R$_2$ are carbobenzyloxy, and R is aminomethyl;
24. Formula VIII wherein R$_1$ and R$_2$ are carbobenzyloxy, and R is aminomethyl;
25. Formula VII wherein R$_1$ and R$_2$ are carbobenzyloxy, and R is propyl;
26. Formula VIII wherein R$_1$ and R$_2$ are carbobenzyloxy, and R is propyl;
27. Formula VII wherein R$_1$ and R$_2$ are carbobenzyloxy, and R is n-pentyl;
28. Formula VIII wherein R$_1$ and R$_2$ are carbobenzyloxy, and R is n-pentyl;
29. Formula VII wherein R$_1$ and R$_2$ are carbobenzyloxy, and R is methylethynyl;
30. Formula VIII wherein R$_1$ and R$_2$ are carbobenzyloxy, and R is methylethynyl;
31. Formula VII wherein R$_1$ and R$_2$ are carbobenzyloxy, and R is n-butyl;
32. Formula VIII wherein R$_1$ and R$_2$ are carbobenzyloxy, and R is n-butyl;
33. Formula VII wherein R$_1$ and R$_2$ are carbobenzyloxy, and R is ethenyloxyethyl;
34. Formula VIII wherein R$_1$ and R$_2$ are carbobenzyloxy, and R is ethenyloxyethyl.

EXAMPLE IV

Preparation of N,N'-dicarbobenzyloxy-4'-(n-butylthiomethyl)-spectinomycin (IVa wherein R$_1$ and R$_2$ are carbobenzyloxy; R is methyl, and T is —S—CH$_2$CH$_2$CH$_2$CH$_2$). See Scheme B steps 2, 3, and 4a or Scheme C step 2.

To a solution of the 4'-enamine, N,N'-dicarbobenzyloxy-4'-dimethylaminomethylenespectinomycin, from Example II above (500 mg, 0.76 mMol) dissolved in methanol (7.5 ml) at pH 4 is added a solution of sodium cyanoborohydride (160 mg, 0.25 mMol) in methanol (2.5 ml) over a period of ten minutes. The pH is maintained at pH 4 by methanolic hydrogen chloride. TLC after one hour shows only the N,N'dicarbobenzyloxy-4'-(dimethylaminomethyl)-spectinomycin (III'' wherein R$_1$ and R$_2$ are carbobenzyloxy, and R is methyl) and 4'-enone, N,N'-dicarbobenzyloxy-4'-methylenespectinomycin, (as is identified in Example III above). Butanethiol (0.5 ml, ~0.4 g, ~4.4 mMol) and triethylamine (0.06 ml) are added, and the reaction is stirred for two more hours at 25° C. The reaction is concentrated and chromatographed on silica gel 60 (45 g) using an acetone:chloroform gradient elution (1:9-2:8). 120 mg, a yield of 22 percent by weight of the N,N'-dicarbobenzyloxy-4'(n-butylthiomethyl)-spectinomycin (IVa wherein $R_1$ and $R_2$ are carbobenzyloxy, R is methyl, and Q is $-S-CH_2CH_2CH_2CH_2$). This compound is identified by comparison to the product in the following Example V.

Following the procedure in Example IV but substituting the appropriate 4'-enamine, N,N'-dicarbobenzyloxy-4'-dimethylaminomethylspectinomycin, as prepared in Example II above (II wherein $R_1$ and $R_2$ are carbobenzyloxy, and R is selected from the group as defined above) and further substituting the appropriate nucleophile for butanethiol the following novel N,N'-di-carbobenzyloxy-4'-(substituted) spectinomycin derivative is prepared.

1. N,N'-dicarbobenzyloxy-4'-(n-butylthiomethyl)-5'-demethylspectinomycin (IVa wherein $R_1$ and $R_2$ are carbobenzyloxy, and R is hydrogen);
2. N,N'-dicarbobenzyloxy-4'-(n-butylthiomethyl)-6'-hydroxyspectinomycin (IVa wherein $R_1$ and $R_2$ are carbobenzyloxy, and R is hydroxymethyl);
3. N,N'-dicarbobenzyloxy-4'-(n-butylthiomethyl)-6'-chlorospectinomycin (IVa wherein $R_1$ and $R_2$ are carbobenzyloxy, and R is chloromethyl);
4. N,N'-dicarbobenzyloxy-4'-(n-butylthiomethyl)-6'-bromospectinomycin) (IVa wherein $R_1$ and $R_2$ are carbobenzyloxy, and R is bromomethyl);
5. N,N'-dicarbobenzyloxy-4'-(n-butylthiomethyl)-6'-n-butylspectinomycin (IVa wherein $R_1$ and $R_2$ are carbobenzyloxy, and R is pentyl);
6. N,N'-dicarbobenzyloxy-4'-(n-butylthiomethyl)-6'-acetoxyspectinomycin (IVa wherein $R_1$ and $R_2$ are carbobenzyloxy, and R is acetoxymethyl);
7. N,N'-dicarbobenzyloxy-4'-(n-butylthiomethyl)-6'-phenylmethoxyspectinomycin (IVa wherein $R_1$ and $R_2$ are carbobenzyloxy, and R is phenylmethoxymethyl);
8. N,N'-dicarbobenzyloxy-4'-(n-butylthiomethyl)-5'-phenylmethoxydesmethylspectinomycin (IVa wherein $R_1$ and $R_2$ are carbobenzyloxy, and R is phenylmethoxy);
9. N,N'-dicarbobenzyloxy-4'-(n-butylthiomethyl)-5'-methoxy-5'-demethylspectinomycin (IVa wherein $R_1$ and $R_2$ are carbobenzyloxy, and R is methoxy);
10. N,N'-dicarbobenzyloxy-4'-(n-butylthiomethyl)-6'-methylspectinomycin (IVa wherein $R_1$ and $R_2$ are carbobenzyloxy, and R is ethyl);
11. N,N'-dicarbobenzyloxy-4'-(n-butylthiomethyl)-6'-methoxyspectinomycin (IVa wherein $R_1$ and $R_2$ are carbobenzyloxy, and R is methoxymethyl);
12. N,N'-dicarbobenzyloxy-4'-(n-butylthiomethyl)-6'-aminospectinomycin (IVa wherein $R_1$ and $R_2$ are carbobenzyloxy, and R is aminomethyl);
13. N,N'-dicarbobenzyloxy-4'-(n-butylthiomethyl)-6'-ethylspectinomycin (IVa wherein $R_1$ and $R_2$ are carbobenzyloxy, and R is propyl);
14. N,N'-dicarbobenzyloxy-4'-(n-butylthiomethyl)-6'-n-pentylspectinomycin (IVa wherein $R_1$ and $R_2$ are carbobenzyloxy, and R is n-hexyl);
15. N,N'-dicarbobenzyloxy-4'-(n-butylthiomethyl)-5'-methylethynyl-5'-demethylspectinomycin (IVa wherein $R_1$ and $R_2$ are carbobenzyloxy, and R is methylethynyl);
16. N,N'-dicarbobenzyloxy-4'-(n-butylthiomethyl)-6'-n-propylspectinomycin (IVa wherein $R_1$ and $R_2$ are carbobenzyloxy, and R is n-butyl);
17. N,N'-dicarbobenzyloxy-4'-(n-butylthiomethyl)-6'-ethenyloxymethylspectinomycin (IVa wherein $R_1$ and $R_2$ are carbobenzyloxy, and R is ethenyloxyethyl);
18. N,N'-dicarbobenzyloxy-4'-(nitrosooxymethyl)-5'-demethylspectinomycin (IVa wherein $R_1$ and $R_2$ are carbobenzyloxy, and R is hydrogen);
19. N,N'-dicarbobenzyloxy-4'-[2-(N-phenyl-N-propylamino)ethyl]-6'-bromospectinomycin (IVa wherein $R_1$ and $R_2$ are carbobenzyloxy, and R is bromomethyl);
20. N,N'-dicarbobenzyloxy-4'-(nitromethyl)-6'-n-butylspectinomycin (IVa wherein $R_1$ and $R_2$ are carbobenzyloxy, and R is pentyl);
21. N,N'-dicarbobenzyloxy-4'-(hydrazinomethyl)-6'-acetoxyspectinomycin (IVa wherein $R_1$ and $R_2$ are carbobenzyloxy, and R is acetoxymethyl);
22. N,N'-dicarbobenzyloxy-4'-(azidomethyl)-6'-phenylmethoxyspectinomycin (IVa wherein $R_1$ and $R_2$ are carbobenzyloxy, and R is phenylmethoxymethyl);
23. N,N'-dicarbobenzyloxy-4'-[2-[[(methylsulfonyl)methyl]amino]-ethyl]-5'demethyl-5'-phenylmethoxydemethylspectinomycin (IVa wherein $R_1$ and $R_2$ are carbobenzyloxy, and R is phenylmethoxy);
24. N,N'-dicarbobenzyloxy-4'-(mercaptomethyl)-5'-demethyl-5'-methoxyspectinomycin (IVa wherein $R_1$ and $R_2$ are carbobenzyloxy, and R is methoxy);
25. N,N'-dicarbobenzyloxy-4'-[(methylthio)methyl]-6'-methylspectinomycin (IVa wherein $R_1$ and $R_2$ are carbobenzyloxy, and R is ethyl);
26. Bis-[N,N'-dicarbobenzyloxy-6'-methoxyspectinomycin-4'-yl]-disulfide (IVa wherein $R_1$ and $R_2$ are carbobenzyloxy, and R is methoxymethyl);
27. N,N'-dicarbobenzyloxy-4'-(2-acetyl-2-propionylethyl-6'-n-pentylspectinomycin (IVa wherein $R_1$ and $R_2$ are carbobenzyloxy, and R is n-hexyl);
28. N,N'-dicarbobenzyloxy-4'-(cyanomethyl)-5'-demethyl-5'-methylethynylspectinomycin (IVa wherein $R_1$ and $R_2$ are carbobenzyloxy, and R is methylethynyl);
29. N,N'-dicarbobenzyloxy-4'-(3-cyanopropyl)-6'-n-propylspectinomycin (IVa wherein $R_1$ and $R_2$ are carbobenzyloxy, and R is n-butyl);
30. N,N'-dicarbobenzyloxy-4'-[2-acetyl-2-[(ethenyloxy)carbonyl]]ethyl-6'-(2-ethenyloxymethylspectinomycin) (III'' wherein $R_1$ and $R_2$ are carbobenzyloxy, and R is ethenyloxyethyl);
31. N,N'-dicarbobenzyloxy-4'-[2,2-bis(ethoxycarbonyl)-5'-demethylspectinomycin (IVa wherein $R_1$ and $R_2$ are carbobenzyloxy, and R is hydrogen);
32. N,N'-dicarbobenzyloxy-4'-(2,2-dimethyl-2-nitroethyl)-6'-hydroxyspectinomycin (IVa wherein $R_1$ and $R_2$ are carbobenzyloxy, and R is hydroxymethyl);
33. N,N'-dicarbobenzyloxy-4'-[2,2-diethyl-2-(methylsulfonyl)-ethyl]-6'-chlorospectinomycin (IVa wherein $R_1$ and $R_2$ are carbobenzyloxy, and R is chloromethyl);
34. N,N'-dicarbobenzyloxy-4'-(2,2-cyano-2-isobutylethyl)-6'-bromospectinomycin (IVa wherein $R_1$ and $R_2$ are carbobenzyloxy, and R is bromomethyl).

EXAMPLE V

Preparation of N,N'-dicarbobenzyloxy-4'-(n-butylthiomethyl)-spectinomycin (IVa wherein $R_1$ and $R_2$ are carbobenzyloxy; R is methyl, and Q is $-S-CH_2CH_2CH_2CH_2$). See Scheme D steps 1 and 2.

N,N-dimethyl(methylene)ammonium chloride

A solution of distilled acetyl chloride (1.50 ml, 1.58 g, 20.0 mMol) in ether (5 ml) is added carefully to a solution of N,N,N',N'-tetramethyldiamino-methane (2.70 ml, 2.02 g, 19.8 mMol) in ether (50 ml). At 25° C. under N₂ atmosphere the product precipitates out immediately as a white solid. After 30 minutes, the solvent is removed with a filter stick, and the solid is washed two times with 25 milliliters of ether. CMR (d₃-acetonitrile). 79.4, 38.8 ppm.

N,N'-dicarbobenzyloxy-4'-(dimethylaminomethyl)-spectinomycin hydrogen chloride (III" wherein $R_1$ and $R_2$ are carbobenzyloxy, and R is methyl)

To the pre-formed reagent described above is added N,N'-dicarbobenzyloxyspectinomycin (III" wherein $R_1$ and $R_2$ are carbobenzyloxy, and R is methyl) (5.0 g, 8.3 mMol), acetonitrile (25 ml) and trifluoroacetic acid (0.5 ml, 0.74 g, 6.5 mMol). The substrate and reagent are stirred at 25° C. until a solution is effected. The reaction is then refluxed for 2.5 hours and cooled to 25° C. before the addition of n-butane thiol.

N,N'-dicarbobenzyloxy-4'-(n-butylthiomethyl)-spectinomycin (IVa wherein $R_1$ and $R_2$ are carbobenzyloxy, and R is methyl)

To the above solution of the N,N'-dicarbobenzyloxy-4'-dimethylaminomethyl)-spectinomycin hydrogen chloride (III" wherein $R_1$ and $R_2$ are carbobenzyloxy, and R is methyl) and the 4'-enone, N,N'-dicarbobenzyloxy-4'-methylenespectinomycin, (I wherein $R_1$ and $R_2$ are carbobenzyloxy, and R is methyl) is added tert-butanol (15 ml) and n-butanethiol (4 ml, 3.2 g, 35.5 mMol). The pH of the reaction mixture is adjusted to between pH 7.5–8.0 with triethylamine. The reaction is stirred at 25° C. for 3.5 hours then placed in the freezer over night. The solution is concentrated to an oil and chromatographed on silica gel 60 with an acetone:-chloroform gradient (1:9→2:8). 3.15 g of the N,N'-dicarbobenzyloxy-4'-(n-butylthiomethyl)-spectinomycin (IVa wherein $R_1$ and $R_2$ are carbobenzyloxy; R is methyl, and T is —S—CH₂CH₂CH₂CH₃). An oil prepared as described above showed the following characteristics.

Mass spec: (mixture of tri- and tetra-TMS):

3×TMS 918 M+, 903

4×TMS 990 M+, 975, 901.

CMR (d₆-acetone): 202.2, 157, 138.0, 129.1, 128.3, 97.2, 92.2, 75.0, 74, 71.4, 67.2, 66.4, 65.7, 60.5, 57.4, 54.1, 33.7, 32.2, 31.4, 26.9, 22.3, 20.1, 13.8 ppm.

PMR (CDCl₃) 7.26 (φ, 10H, s), 5.06 (OCH₂, 4H, s), 3.34–4.65 (CHOH, 11H, m), 3.04 (NCH₃, 6H, d), 2.71 (CH₂—S, 2H, d), 2.53 (S—CH₂, 2H, t), 1.44 (CH₃, 3H, d), 1.65–1.25 (CH₂, 5H, m), 0.89 (CH₃, 3H, t).

$[\alpha]_D = +3°$.

I.R. 3400, 1685, 1585, 1500, 1545, 1345, 1165, 1115, 1080, 1060, 1030, 770, 735, 695.

Following the procedure in Example V but substituting the appropriate analog of N,N'-dicarbobenzyloxy-4'-(dimethylaminomethyl)-spectinomycin hydrogen chloride (III" wherein $R_1$ and $R_2$ are carbobenzyloxy, and R is selected from the group as defined above), and again further substituting the appropriate nucleophile as defined above is substituted for butanethiol the following N,N'-dicarbobenzyloxy-4'-(substituted)-spectinomycin derivative is prepared.

1. N,N'-dicarbobenzyloxy-4'-(n-butythiomethyl)-5'-demethylspectinomycin (IVa wherein $R_1$ and $R_2$ are carbobenzyloxy, and R is hydrogen);
2. N,N'-dicarbobenzyloxy-4'-(n-butylthiomethyl)-6'-hydroxyspectinomycin (IVa wherein $R_1$ and $R_2$ are carbobenzyloxy, and R is hydroxymethyl);
3. N,N'-dicarbobenzyloxy-4'-(n-butylthiomethyl)-6'-chlorospectinomycin (IVa wherein $R_1$ and $R_2$ are carbobenzyloxy, and R is chloromethyl);
4. N,N'-dicarbobenzyloxy-4'-(n-butylthiomethyl)-6'-bromospectinomycin) (IVa wherein $R_1$ and $R_2$ are carbobenzyloxy, and R is bromomethyl);
5. N,N'-dicarbobenzyloxy-4'-(n-butylthiomethyl)-6'-n-butylspectinomycin (IVa wherein $R_1$ and $R_2$ are carbobenzyloxy, and R is pentyl);
6. N,N'-dicarbobenzyloxy-4'-(n-butylthiomethyl)-6'-acetoxyspectinomycin (IVa wherein $R_1$ and $R_2$ are carbobenzyloxy, and R is acetoxymethyl);
7. N,N'-dicarbobenzyloxy-4'-(n-butylthiomethyl)-6'-phenylmethoxyspectinomycin (IVa wherein $R_1$ and $R_2$ are carbobenzyloxy, and R is phenylmethoxymethyl);
8. N,N'-dicarbobenzyloxy-4'-(n-butylthiomethyl)-5'-demethyl-5'-phenylmethoxyspectinomycin (IVa wherein $R_1$ and $R_2$ are carbobenzyloxy, and R is phenylmethoxy);
9. N,N'-dicarbobenzyloxy-4'-(n-butylthiomethyl)-5'-demethyl-5'-methoxyspectinomycin (IVa wherein $R_1$ and $R_2$ are carbobenzyloxy, and R is methoxy);
10. N,N'-dicarbobenzyloxy-4'-(n-butylthiomethyl)-6'-methylspectinomycin (IVa wherein $R_1$ and $R_2$ are carbobenzyloxy, and R is ethyl);
11. N,N'-dicarbobenzyloxy-4'-(n-butylthiomethyl)-6'-methoxyspectinomycin (IVa wherein $R_1$ and $R_2$ are carbobenzyloxy, and R is methoxymethyl);
12. N,N'-dicarbobenzyloxy-4'-(n-butylthiomethyl)-6'-aminospectinomycin (IVa wherein $R_1$ and $R_2$ are carbobenzyloxy, and R is aminomethyl);
13. N,N'-dicarbobenzyloxy-4'-(n-butylthiomethyl)-6'-ethylspectinomycin (IVa wherein $R_1$ and $R_2$ are carbobenzyloxy, and R is propyl);
14. N,N'-dicarbobenzyloxy-4'-(n-butylthiomethyl)-6'-n-pentylspectinomycin (IVa wherein $R_1$ and $R_2$ are carbobenzyloxy, and R is n-hexyl);
15. N,N'-dicarbobenzyloxy-4'-(n-butylthiomethyl)-5'-demethyl-5'-methylethynylspectinomycin (IVa wherein $R_1$ and $R_2$ are carbobenzyloxy, and R is methylethynyl);
16. N,N'-dicarbobenzyloxy-4'-(n-butylthiomethyl)-6'-n-propylspectinomycin (IVa wherein $R_1$ and $R_2$ are carbobenzyloxy, and R is n-butyl);
17. N,N'-dicarbobenzyloxy-4'-(n-butylthiomethyl)-6'-ethenyloxymethylspectinomycin (IVa wherein $R_1$ and $R_2$ are carbobenzyloxy, and R is ethenyloxyethyl);
18. N,N'-dicarbobenzyloxy-4'-(nitrosooxymethyl)-5'-demethylspectinomycin (IVa wherein $R_1$ and $R_2$ are carbobenzyloxy, and R is hydrogen);
19. N,N'-dicarbobenzyloxy-4'-[2-(N-phenyl-N-propylamino)-ethyl]-6'-bromospectinomycin) (IVa wherein $R_1$ and $R_2$ are carbobenzyloxy, and R is bromomethyl);
20. N,N'-dicarbobenzyloxy-4'-(nitromethyl)-6'-n-butylspectinomycin (IVa wherein $R_1$ and $R_2$ are carbobenzyloxy, and R is pentyl);
21. N,N'-dicarbobenzyloxy-4'-(hydrazinomethyl)-6'-acetoxyspectinomycin (IVa wherein $R_1$ and $R_2$ are carbobenzyloxy, and R is acetoxymethyl);

22. N,N'-dicarbobenzyloxy-4'-(azidomethyl)-6'-phenylmethoxyspectinomycin (IVa wherein R₁ and R₂ are carbobenzyloxy, and R is phenylmethoxymethyl);
23. N,N'-dicarbobenzyloxy-4'-[2-[[(methylsulfonyl)methyl]amino]-ethyl]-5'-phenylmethoxydesmethylspectinomycin (IVa wherein R₁ and R₂ are carbobenzyloxy, and R is phenylmethoxy);
24. N,N'-dicarbobenzyloxy-4'-(mercaptomethyl)-5'-demethyl-5'-methoxyspectinomycin (IVa wherein R₁ and R₂ are carbobenzyloxy, and R is methoxy);
25. N,N'-dicarbobenzyloxy-4'-[(methylthio)methyl]-6'-methylspectinomycin (IVa wherein R₁ and R₂ are carbobenzyloxy, and R is ethyl);
26. Bis-[N,N'-dicarbobenzyloxy-6'-methoxyspectinomycin-4'-yl]-disulfide (IVa wherein R₁ and R₂ are carbobenzyloxy, and R is methoxymethyl);
27. N,N'-dicarbobenzyloxy-4'-(2-acetyl-2-propionylethyl)-6'-n-pentylspectinomycin (IVa wherein R₁ and R₂ are carbobenzyloxy, and R is n-hexyl);
28. N,N'-dicarbobenzyloxy-4'-(cyanomethyl)-5'-demethyl-5'-methylethynylspectinomycin (IVa wherein R₁ and R₂ are carbobenzyloxy, and R is methylethynyl);
29. N,N'-dicarbobenzyloxy-4'-(3-cyanopropyl)-6'-n-propylspectinomycin (IVa wherein R₁ and R₂ are carbobenzyloxy, and R is n-butyl);
30. N,N'-dicarbobenzyloxy-4'-(2-acetyl-2-[(ethenyloxy)carbonyl]-ethyl-6'-(2-ethenyl)oxymethylspectinomycin (III″ wherein R₁ and R₂ are carbobenzyloxy, and R is 2-ethenyloxyethyl);
31. N,N'-dicarbobenzyloxy-4'-[(2,2-bis(ethoxycarbonyl)ethyl-5'-demethylspectinomycin (IVa wherein R₁ and R₂ are carbobenzyloxy, and R is hydrogen);
32. N,N'-dicarbobenzyloxy-4'-(2,2-dimethyl-2-nitroethyl)-6'-hydroxyspectinomycin (IVa wherein R₁ and R₂ are carbobenzyloxy, and R is hydroxymethyl);
33. N,N'-dicarbobenzyloxy-4'-[2,2-diethyl-2-(methylsulfonyl)-ethyl]-6'-chlorospectinomycin (IVa wherein R₁ and R₂ are carbobenzyloxy, and R is chloromethyl);
34. N,N'-dicarbobenzyloxy-4'-(2,2-cyano-2-isobutylethyl)-6'-bromospectinomycin (IVa wherein R₁ and R₂ are carbobenzyloxy, and R is bromomethyl).

EXAMPLE VI

Preparation of 4'-(n-butylthiomethyl)-spectinomycin (IVb wherein Q is —S—CH₂CH₂CH₂CH₂). See deprotection steps of each Scheme A through D.

The N,N'-dicarbobenzyloxy-4'-(n-butylthiomethyl)-spectinomycin (IVa wherein R₁ and R₂ are carbobenzyloxy; R is methyl, and Q is —S—CH₂CH₂CH₂CH₃) (150 mg, 0.21 mMol) from Example V is stirred with thioanisole (1 ml) and distilled trifluoroacetic acid (4 ml) at 25° C. for four to five hours. The reaction is concentrated, and the product is precipitated with ether (20 ml) to a gum. The solid is washed with ether (25 ml) and redissolved in isopropanol (7 ml). Conversion to the dihydrochloride salt with 1N HCl in isopropanol gives a white solid precipitate which is filtered to give 65 mg (61 percent) of 4'-(n-butylthiomethyl)-spectinomycin (IVb wherein Q is —S—CH₂—CH₂—CH₂—CH₂). It was identified as follows:

CMR (D₂O) 94.1, 93.0, 73.1, 70.8, 67.0, 66.7, 62.6, 60.5, 59.6, 49.8, 33.2, 31.9, 31.3, 27.2, 22.4, 19.6, 14.1 ppm. High resolution mass spec. (tri-TMS) calcd for $C_{28}H_{58}N_2O_7S_1Si_3$=650.3272. Found:=650.3252.

Following the procedure in Example VI but substituting the appropriate N,N'-dicarbobenzyloxy-4'-(substituted)-spectinomycin (IVa wherein R₁ and R₂ are carbobenzyloxy; R and Q are selected from the group as defined above), the following spectinomycin derivative is prepared.

1. 4'-(n-butylthiomethyl)-5'-demethylspectinomycin (IVb wherein R is hydrogen);
2. 4'-(n-butylthiomethyl)-6'-hydroxyspectinomycin (IVb wherein R is hydroxymethyl);
3. 4'-(n-butylthiomethyl)-6'-chlorospectinomycin (IVb wherein R is chloromethyl);
4. 4'-(n-butylthiomethyl)-6'-bromospectinomycin) (IVb wherein R is bromomethyl);
5. 4'-(n-butylthiomethyl)-6'-n-butylspectinomycin (IVb wherein R is pentyl);
6. 4'-(n-butylthiomethyl)-6'-acetoxyspectinomycin (IVb wherein R is acetoxymethyl);
7. 4'-(n-butylthiomethyl)-6'-phenylmethoxyspectinomycin (IVb wherein R is phenylmethoxymethyl);
8. 4'-(n-butylthiomethyl)-5'-demethyl-5'-phenylmethoxyspectinomycin (IVb wherein R is phenylmethoxy);
9. 4'-(n-butylthiomethyl)-5'-demethyl-5'-methoxyspectinomycin (IVb wherein R is methoxy);
10. 4'-(n-butylthiomethyl)-6'-methylspectinomycin (IVb wherein R is ethyl);
11. 4'-(n-butylthiomethyl)-6'-methoxyspectinomycin (IVb wherein R is methoxymethyl);
12. 4'-(n-butylthiomethyl)-6'-aminospectinomycin (IVb wherein R is aminomethyl);
13. 4'-(n-butylthiomethyl)-6'-ethylspectinomycin (IVb wherein R is propyl);
14. 4'-(n-butylthiomethyl)-6'-n-heptylspectinomycin (IVb wherein R is n-hexyl);
15. 4'-(n-butylthiomethyl)-5'-demethyl-5'-methylethynylspectinomycin (IVb wherein R is methylethynyl);
16. 4'-(n-butylthiomethyl)-6'-n-propylspectinomycin (IVb wherein R is n-butyl);
17. 4'-(n-butylthiomethyl)-6'-ethenyloxymethylspectinomycin (IVb wherein R is ethenyloxyethyl);
18. 4'-(oxynitrosooxymethyl)-5'-demethyl-5'-spectinomycin (IVb wherein R is hydrogen);
19. 4'-(methylaminomethyl)-6'-hydroxyspectinomycin (IVb wherein R is hydroxymethyl);
20. 4'-[(ethylmethylamino)methyl]-6'-chlorospectinomycin (IVb wherein R is chloromethyl);
21. 4'-[2'-(N-phenyl-N-propylamino)ethyl]-6'-bromospectinomycin (IVb wherein R is bromomethyl);
22. 4'-(nitromethyl)-6'-n-butylspectinomycin (IVb wherein R is pentyl);
23. 4'-(hydrazinomethyl)-6'-acetoxyspectinomycin (IVb wherein R is acetoxymethyl);
24. 4'-(azidomethyl)-6'-phenylmethoxyspectinomycin (IVb wherein R is phenylmethoxymethyl);
25. 4'-[2-[[(methylsulfonyl)methyl]amino]ethyl]-5'-demethyl-5'-phenylmethoxyspectinomycin (IVb wherein R is phenylmethoxy);
26. 4'-(mercaptomethyl)-5'-demethyl-5'-methoxyspectinomycin (IVb wherein R is methoxy);
27. 4'-[(methylthio)methyl]-6'-methylspectinomycin (IVb wherein R is ethyl);
28. Bis-(6'-methoxyspectinomycin-4'-yl)disulfide (IVb wherein R is methoxymethyl);
29. 4'-(n-butyl)-6'-aminospectinomycin (IVb wherein R₁ and R₂ are carbobenzyloxy, and R is aminomethyl);
30. 4'-[(methylethynyl)methyl]-6'-ethylspectinomycin (IVb wherein R is propyl);

31. 4'-(2-acetyl-2-propionylethyl)-6'-n-pentylspectinomycin (IVb wherein R is n-hexyl);
32. 4'-(cyanomethyl)-5'-demethyl-5'-methylethynylspectinomycin (IVb wherein R is methylethynyl);
33. 4'-(3-cyanopropyl)-6'-n-propylspectinomycin (IVb wherein R is n-butyl);
34. 4'-(2-acetyl-2-[(ethenyloxy)carbonyl]ethyl-6'-(2-ethenyl)oxymethylspectinomycin (IVb wherein R is ethenyloxyethyl);
35. 4'-[2,2-bis(ethoxycarbonyl)ethyl]-5'-demethylspectinomycin (IVb wherein R is hydrogen);
36. 4'-(2,2-dimethyl-2-nitroethyl)-6'-hydroxyspectinomycin (IVb wherein R is hydroxymethyl);
37. 4'-[2,2-diethyl-2-(methylsulfonyl)ethyl]-6'-chlorospectinomycin (IVb wherein R is chloromethyl);
38. 4'-(2,2-cyano-2-isobutylethyl)-6'-bromospectinomycin (IVb wherein R is bromomethyl).

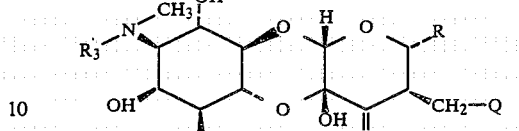

-continued
SCHEME A
Enone 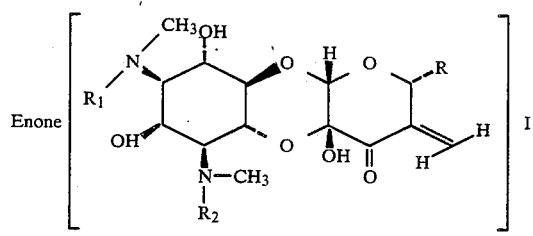 I
step (3a) nucleophile Et₃N
step (3) dimerization
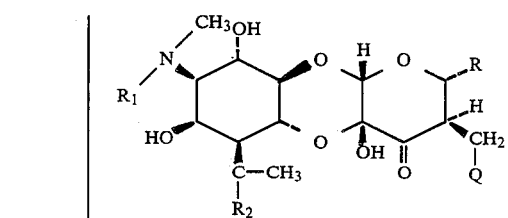 IVa
Dimer VII 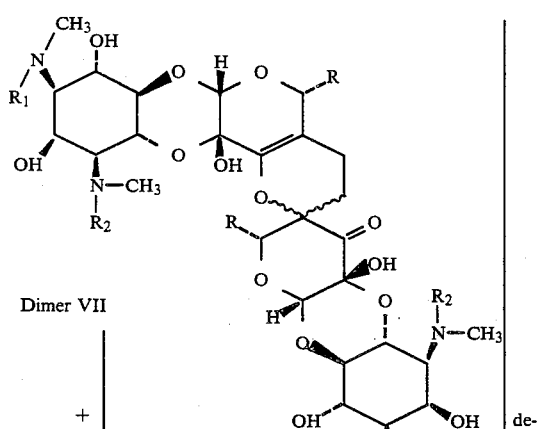
+
deprotection
step (4)
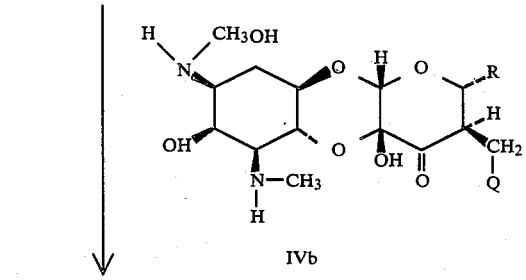
IVb
-continued
SCHEME A
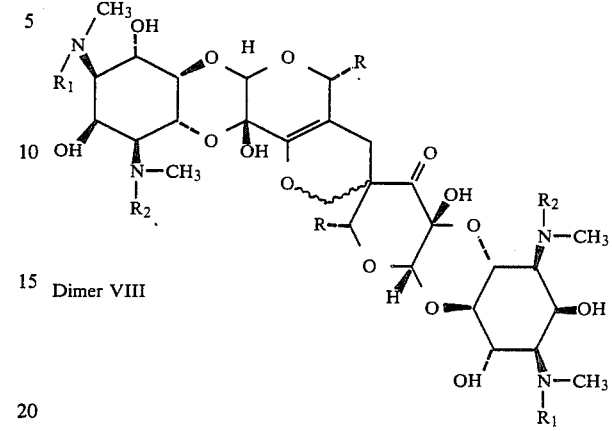
Dimer VIII
SCHEME B
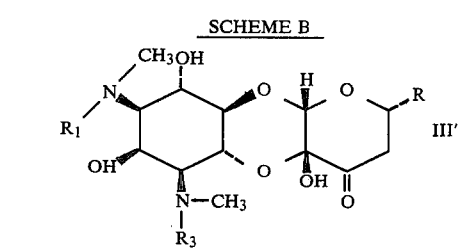 III'
step 1 TFA/DMF
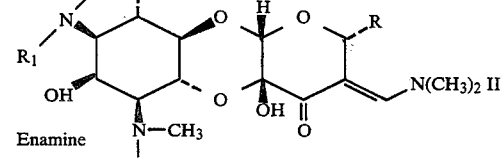 II
Enamine
step 2 NaCNBH₃ H⁺ MeOH
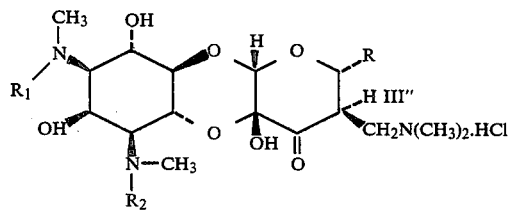 III''
step 3 H⁺ —H⁺

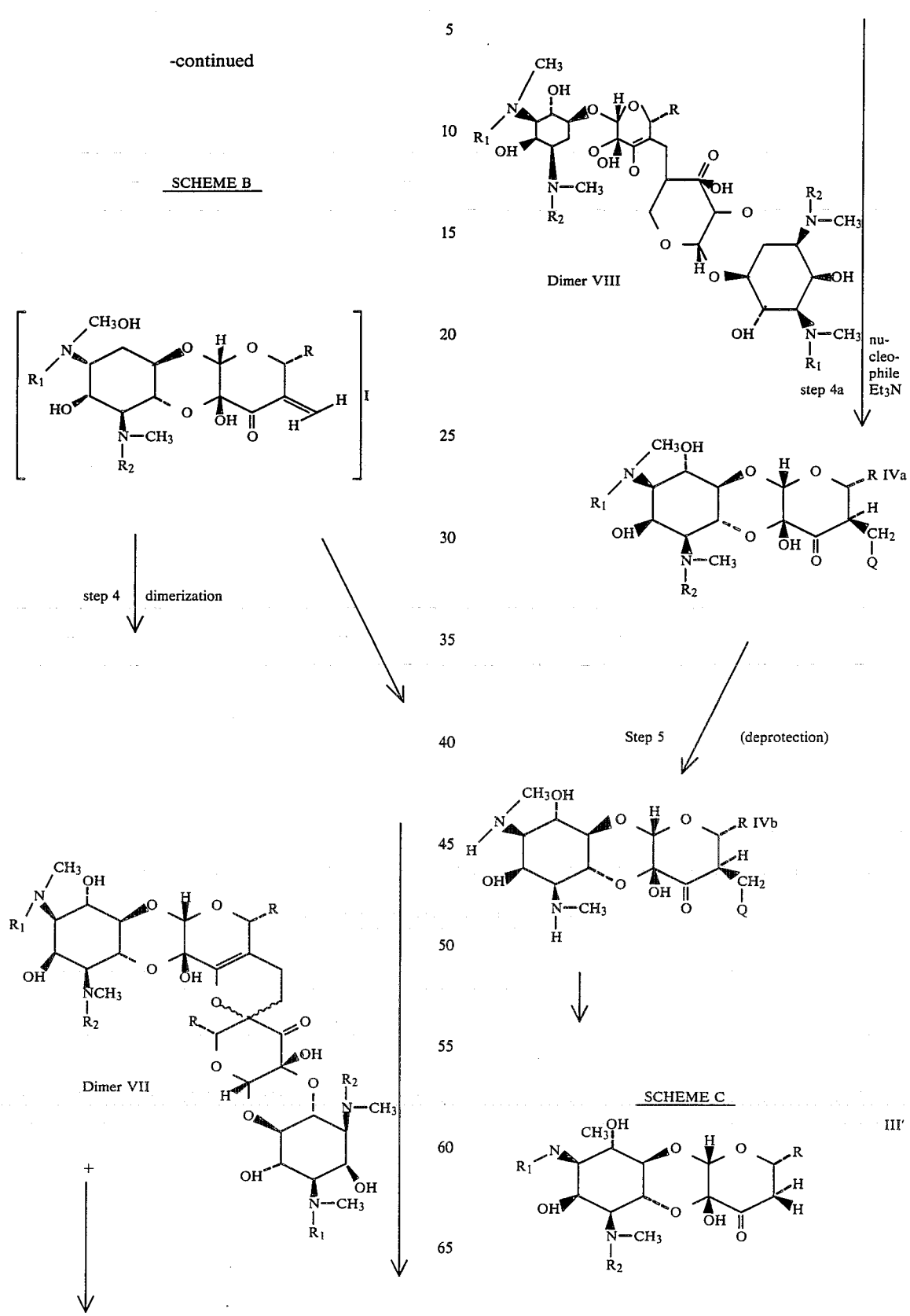

-continued
SCHEME C

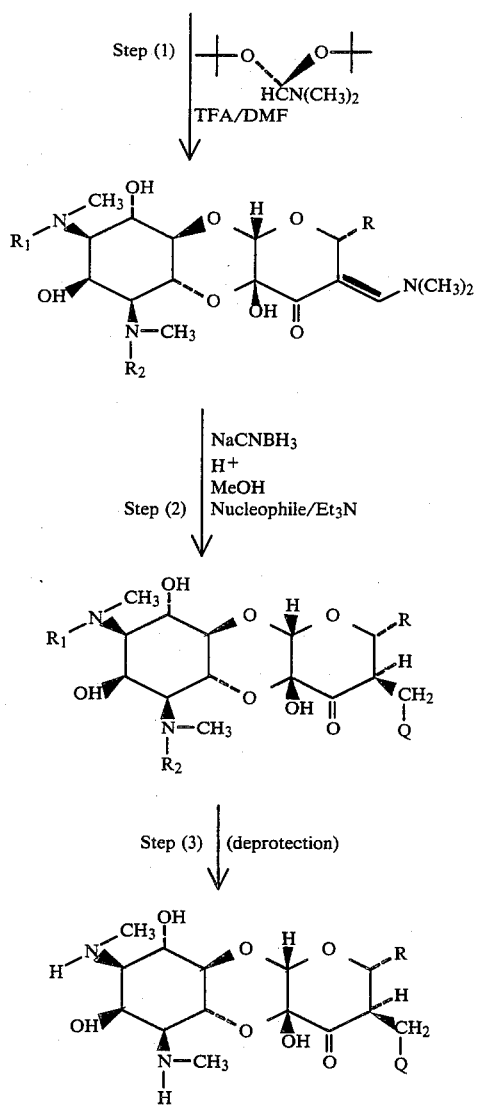

SCHEME D

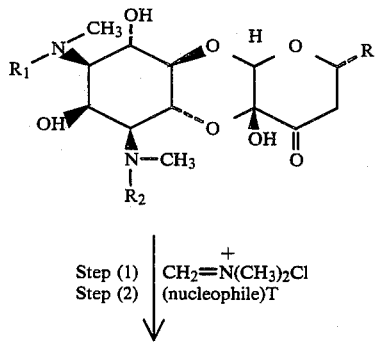

Step (1) CH$_2$=N(CH$_3$)$_2$Cl$^+$
Step (2) (nucleophile)T

-continued
SCHEME D

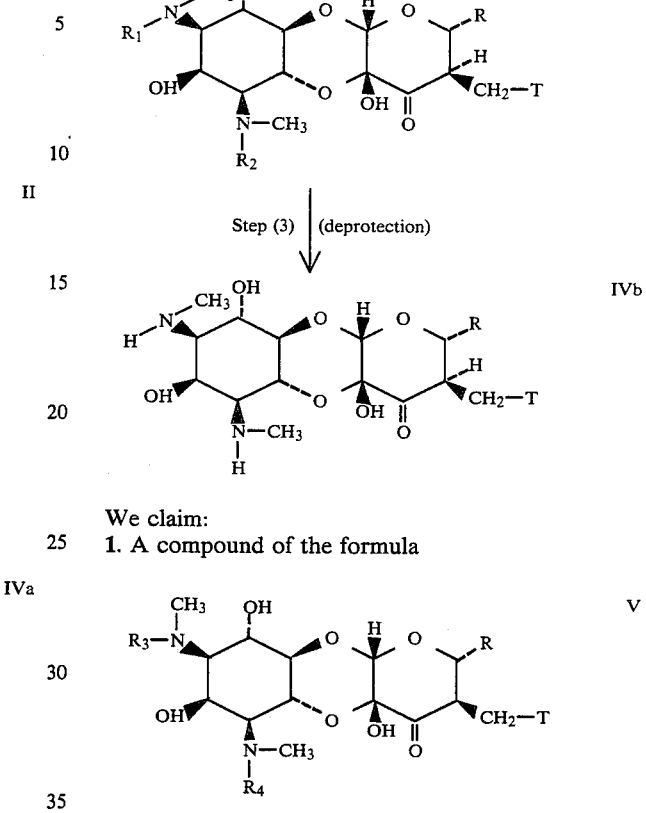

We claim:

1. A compound of the formula

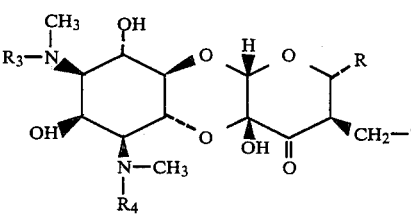

wherein R$_3$ and R$_4$ are the same and are hydrogen or blocking groups;

T is selected from the group consisting of —OY, —CHR$_5$C(O)R$_6$, [—NH$_2$,] —NHR$_5$, —NR$_5$R$_6$, —NO$_2$, —NHNH$_2$, —N$_3$, —NR$_5$SO$_2$R$_6$, —SH, —SR$_5$, —S—SM$_2^+$, —CH[C(O)R$_5$]C(O)R$_6$], —C≡N, —CHC(N)R$_5$, —CH[C(O)R$_5$][-C(O)OR$_6$], —CH[C(O)OR$_5$][C(O)OR$_6$], —CR$_5$R$_6$NO$_2$, —CR$_5$R$_6$SO$_2$R$_7$, —CR$_5$C(N)C(N), wherein Y is aryl or —CR$_5$=CHR$_6$ or —N=O, and R$_5$, R$_6$, and R$_7$ are the same or different and are lower alkyl or aryl with the proviso that when T is —NHR$_5$, —NR$_5$R$_6$ or —OCR$_5$=CHR$_6$, R$_5$ and R$_6$ are aryl;

wherein

R is hydrogen, alkyl of from C$_1$ to C$_{20}$, inclusive, lower alkenyl, lower haloalkyl, lower aminoalkyl, lower alkynyl or —(CH$_2$)$_n$—OX wherein X is selected from the group consisting of hydrogen, lower alkyl, lower alkenyl, benzyl, and acyl wherein n is an integer of zero to four with the proviso that when n is zero —OX cannot be hydroxy and biologically acceptable salts thereof.

2. A compound of claim 1 wherein R$_3$ and R$_4$ are a blocking group.

3. A compound of claim 1 wherein R$_3$ and R$_4$ are hydrogen.

* * * * *